United States Patent [19]

Russell et al.

[11] Patent Number: 5,013,304
[45] Date of Patent: May 7, 1991

[54] INTRAVASCULAR CATHETER ASSEMBLY

[75] Inventors: John P. Russell, Centerpoint; Terry Carroll, Dora; Sam Miller, Birmingham, all of Ala.

[73] Assignee: BFD, Inc., Gardendale, Ala.

[21] Appl. No.: 313,465

[22] Filed: Feb. 22, 1989

[51] Int. Cl.⁵ .............................................. A61M 5/00
[52] U.S. Cl. ...................... 604/167; 604/164
[58] Field of Search ............... 604/162, 110, 164–169, 604/171, 198, 263

[56] References Cited

U.S. PATENT DOCUMENTS

| | | | |
|---|---|---|---|
| 3,572,334 | 3/1971 | Petterson | 604/162 |
| 4,193,399 | 3/1980 | Robinson | 604/168 |
| 4,224,943 | 9/1980 | Johnson et al. | 604/164 |
| 4,610,665 | 9/1986 | Matsumoto et al. | 604/256 |
| 4,747,831 | 5/1988 | Kulli | 604/198 |
| 4,762,516 | 8/1988 | Luther et al. | 604/164 |
| 4,772,265 | 9/1988 | Walter | 604/168 |
| 4,781,692 | 11/1988 | Jagger et al. | 604/164 |
| 4,834,718 | 5/1989 | McDonald | 604/164 |
| 4,846,805 | 7/1989 | Sitar | 604/165 |
| 4,850,961 | 7/1989 | Wanderer et al. | 604/164 |
| 4,917,669 | 4/1990 | Bonaldo | 604/164 |
| 4,935,010 | 6/1990 | Cox et al. | 604/167 |
| 4,944,728 | 7/1990 | Carrell et al. | 604/164 |

Primary Examiner—Stephen C. Pellegrino
Assistant Examiner—Ralph A. Lewis
Attorney, Agent, or Firm—George A. Bode

[57] ABSTRACT

An intravascular catheter assembly includes a catheter needle sheath having a retractable needle which is moved upon slidable movement of a handle member that is slidably mounted in the housing of the catheter needle sheath. The catheter needle safety sheath is insertable into a catheter or into a catheter adapter and backflow device which is in turn insertable into the catheter. The backflow device includes an elastomeric diaphragm disposed therein which re-seals upon withdrawal of the needle therefrom and advantageously prevents excessive fluid leakage from the catheter. The catheter needle safety sheath provides an improved means for disposing of the used needle since the handle member may be slidably moved in a rearward direction so as to retract the needle within the sheath. Both the catheter needle safety sheath as well as the catheter adapter and backflow device prevent unnecessary exposure to bodily fluids which may transmit diseases and thereby enhance the safety of the operators of these devices.

5 Claims, 2 Drawing Sheets

INTRAVASCULAR CATHETER ASSEMBLY

BACKGROUND OF THE INVENTION

1. Field of the Invention

The present invention relates to an intravascular catheter assembly and more particularly to an improved intravascular catheter assembly which provides for fluid connection with various types of fluid conducting devices and which includes a safety sheath that houses a retractable needle and a backflow device that includes an improved self-closing valve member.

2. Description of Related Art

In conventional practice, an intravascular catheter is introduced into a vein of a person by using a sharp hollow bore needle within the bore of the catheter. The hollow bore needle acts as a sharp introducing instrument over which the catheter may be advanced into the vein of the patient. When the needle is inserted, blood flows back through the needle, usually into a small collection container for the blood. When the introducing needle is withdrawn from the catheter and the catheter is moved further into the patient's vein, excessive bleeding and other fluid leakage often occurs during the period of time before the catheter is connected to other equipment which controls the backflow of blood into the catheter. Also, the introducing needle must be quickly and safely disposed of. A common practice during this period between withdrawal of the needle used to introduce the catheter into the vein and connection of the catheter to equipment having a blood flow control device is for the operator to palpate the vein into which the catheter is introduced at the skin's surface immediately ahead of the catheter tip. During palpatation of the vein, the operator compresses the vein into which the catheter has been introduced to prevent or reduce blood flow. However, this procedure is inconvenient in that it necessitates either multiple operators or a single operator who must manipulate with only one hand both the safe withdrawal and disposal of the needle, as well as the connection of the catheter to equipment with fluid control devices. This may be especially difficult when a combative patient is being transported in an ambulance or other emergency vehicle and an intravenous (I.V.) drip set must be started to control the patient's condition. If the patient struggles and the I.V. set comes loose from the catheter, excessive bleeding from the catheter results which can frighten the patient and intensify psychological fear, pain, and emotion.

Very dangerous situations may also arise when a conventional catheter is used on a diseased person who has hepatitis, meningitis, or AIDS or other diseases transmitted by blood. When the sharp, elongated needle used to introduce the catheter into the patient's vein is withdrawn and the catheter is moved further into the vein, the bleeding and fluid leakage from the catheter may expose the operator to contact the patient's blood thus resulting in the possible transmission of the disease carried by the patient to the personnel attending the patient. Further, if the introducing needle is not safely and quickly disposed of, the needle itself may be accidently caused to prick the operator or other personnel involved in disposing of used equipment, such as the needle.

Various attempts have been made to incorporate fluid control devices into catheters in order to control the fluid loss from the catheter. These devices include sealing members made of elastomeric material having a perforation formed therein which re-seals because of the structural confinement of the elastic material and are disclosed, for example, in U.S. Pat. Nos. 3,853,127; 4,177,814; and 4,626,245. Attempts have also been made at providing a means for shielding a needle used in venipuncture as disclosed in U.S. Pat. Nos. 3,595,230; 4,676,783; 4,747,831; and 4,643,199. These conventional devices have not solved all of the problems described above and often are expensive and cumbersome to manufacture. Therefore, there is a need for an improved intravascular catheter assembly having an improved backflow device and an improved needle sheath which solves the above-noted problems and which has a simplified structure so as to be advantageous for manufacture.

SUMMARY OF THE INVENTION

Therefore, it is an object of the present invention to provide an improved intravascular catheter assembly which may be connected in fluid communication with diverse types of fluid conducting devices to conduct fluid into and out of a patient with a single entry into the patient's vein.

Another object of the present invention is to provide a catheter assembly which has an improved self-closing valve that eliminates fluid leakage from the catheter to prevent exposure to infectious diseases such as hepatitis, meningitis, and AIDS.

A further object of the present invention is to provide an improved catheter assembly which includes a safety sheath having a retractable needle which allows for fast and safe disposal of the needle after it is used and which is disposable and inexpensive to manufacture, store, and use. Still, another object of the present invention is to provide an improved catheter assembly which is designed to be easily utilized by operators, for both single and multiple blood samplings, as well as for single and multiple injections of therapeutic fluids into a patient.

The foregoing objects and others are accomplished in accordance with the present invention, generally speaking, by providing an apparatus which includes a catheter member having a plastic needle tube for receiving a needle therethrough for insertion into a vein, a catheter passageway, and a rearwardly opening hub member; and a catheter adapter and backflow device having a front adapter end for insertion into said rearwardly opening hub member in a fluid tight manner, an adapter cavity with said backflow device for fluidly communicating with said catheter member, a rear adapter hub member, and a self-closing valve member for preventing fluid leakage from said catheter member which is disposed in said catheter adapter between said adapter cavity and said adapter hub member, said self-closing valve member comprising an elastomeric diaphragm which re-seals by a return of the diaphragm material to its original position so as to fill puncture openings caused by a needle, wherein said backflow device receives a needle through said self-closing valve for fluid communication therewith; and a catheter needle safety sheath having a tapered front end for insertion into said rear adapter hub member, an elongated hollow sheath housing which includes an elongated slot formed therein, a retractable needle slidably disposed in said sheath housing, a needle hub member mounted on a rearward end of said needle, a fin-shaped handle mounted on said needle hub member, said handle projecting out of said slot for slidably moving said needle so that it projects out of said front end or retract into said sheath housing, and a needle hub support member mounted on a rearward end of said needle hub member and slidably disposed within said sheath housing for slidably supporting said handle and said needle.

Further scope of the applicability of the present invention will become apparent from the detailed description and drawings provided below. However, it should be understood that the detailed description and drawings, as well as the specific examples, while indicating preferred embodiments of the present invention, are given by way of illustration only, since various changes and modifications within the spirit and scope of the invention become apparent to those skilled in the art from this description.

BRIEF DESCRIPTION OF THE DRAWINGS

The invention is further illustrated by the accompanying drawings wherein like elements are given like reference numerals and wherein.

DETAILED DESCRIPTION OF THE INVENTION

Figure 1:
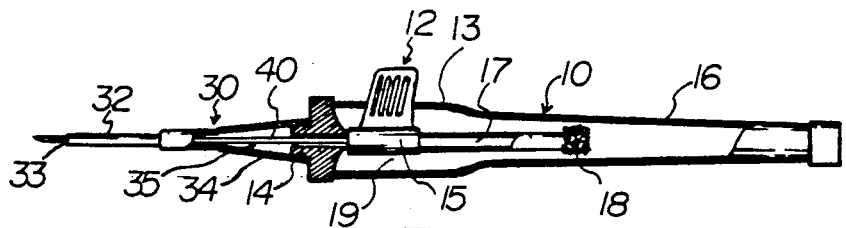
FIG. 1 is a side view of the catheter needle sheath and catheter of a first embodiment of the present invention.
Figure 2:
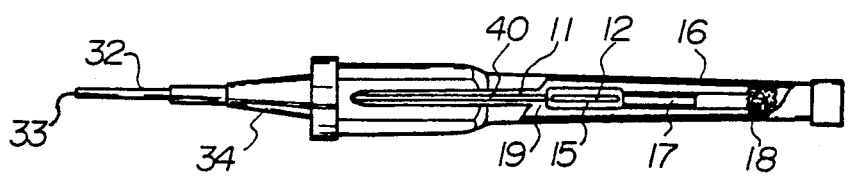
FIG. 2 is a top view of the catheter needle sheath and catheter of a first embodiment of the present invention, wherein the needle is retracted into the needle sheath.
Figure 3:
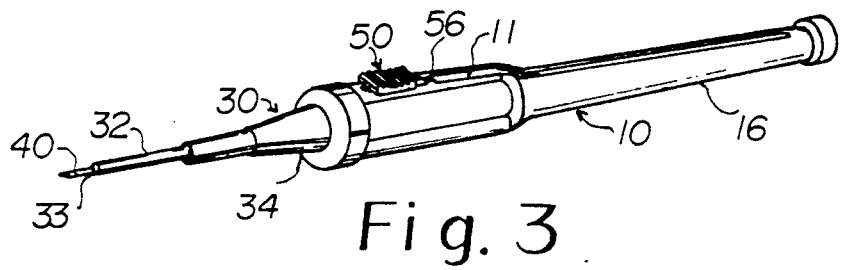
FIG. 3 is a perspective view of the catheter needle sheath and catheter of a second embodiment of the present invention, wherein the needle is projecting out of the catheter needle sheath.

FIGS. 1 and 2 illustrate one preferred embodiment of the intravascular catheter assembly of the present invention. In this embodiment, a catheter needle safety sheath 10 is connected to a catheter 30 so as to be in fluid communication therewith. The needle safety sheath 10 includes a movable fin-shaped handle member 12 which slidably moves along an elongated slot 11 formed in the sheath housing 13 as shown in FIGS. 1 and 2. A sharp, elongated hollow needle 40 is mounted on the handle member 12 by means of a needle hub member 15 within the sheath cavity 19. The needle hub member 15 includes a needle hub flash chamber 17 in fluid communication with the needle 40. The flash chamber 17 is used to view blood return when the vein is stuck and is in turn connected to a needle hub end member 18 which slidably fits within the cavity of the sheath rear portion 16 so as to properly vent the flash chamber 17. The flash chamber 17 is hollow and is formed from transparent material, such as clear plastic tube material. The flexibility of the material allows for the flash chamber to be crushed in the sheath rear portion 16 so that the chamber, when filled with blood, is sealed and so that the dimensions of the rear portion 16 may be relatively small. The needle hub end member 18 is used to house cotton and/or paper mesh filter material which allows air to pass or vent properly through the needle and flash chamber after the vein is stuck. End member 18 acts as a filter so that blood and air flow through the needle. Upon blood contacting the filter material of end member 18 swelling occurs thereby sealing the end of flash chamber 17 and preventing the blood or other fluids from entering the sheath.

The catheter needle safety sheath 10 includes a tapered, front end 14 which is inserted in a fluid tight manner into a rearwardly opening hub member 34 of the catheter 30. The needle 40 projects through a catheter passageway 35 and a bore 33 of a plastic needle tube 32 of the catheter 30.

During operation, the handle member 12 is placed in a forward position so that the needle 40 projects through the plastic needle tube 32 as shown in FIGS. 1 and 2. After placement of the catheter in the patient's vein, the handle member 12 is then slidably retracted by rearward movement of the handle member 12 in the direction of the sheath rear portion 16 so as to retract the needle 40 within the needle safety sheath housing 13 so that the end of the needle is moved beyond a convex-shaped retraction hole 13a which prevents the needle from being positioned to accidently again project through the hole since the needle tends to remain in the peripheral portion of the convex-shaped retraction hole 13a. The front end 14 of the sheath may be disengaged from the catheter 30.

Figure 4A:
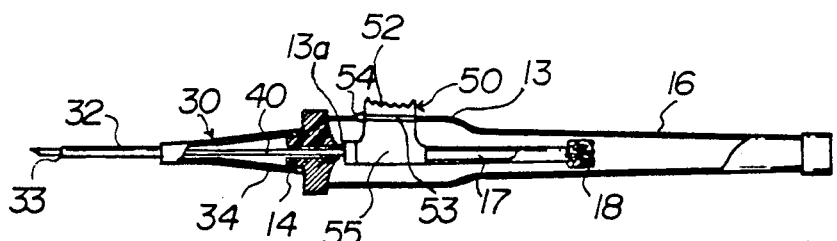
FIGS. 4(a), 4(b), and 4(c) depict a side view, a tab-shaped handle, and a top view of a second embodiment of the catheter needle sheath and catheter of the present invention.
Figure 4B:
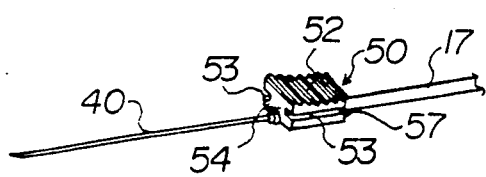
Figure 4C:
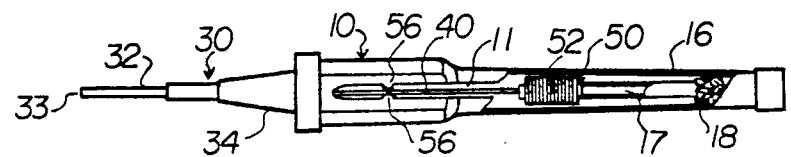

A second embodiment of the present invention is illustrated in FIGS. 3, 4(a), 4(b), and 4(c) which show a tab-shaped handle member 50 which serves generally the same functions as the fin-shaped handle member 12 described above. The tab-shaped handle member 50 is connected to an elongated hollow needle 40 by means of a needle hub member 55 which is in turn connected to a flash chamber 17 and a needle hub end member 18 as shown in FIG. 4(a). The tab-shaped handle member 50 further includes a roughened upper surface 52 on which an operator's thumb or forefinger is placed for convenient slidable movement of the handle member 50 along an elongated slot 11. Side slots 53 of the handle member 50 slidably engage housing 13. Stop tab members 56 are fixed on opposite sides of the elongated slot 11 so as to engage the rearward end 57 of the tab-shaped handle member 50 for locking the needle 40 into the forward position after slidable movement thereof by means of the handle member 50. The tab members 56 comprise two half moon shaped members which extend into the elongated slot 11. A wedge member 54 is disposed at the front portion of the handle member 50 so as to provide for a forward position lock of the handle member by frictional engagement with the front tapered portion 11a of the engagement slot 11.

Figure 5:
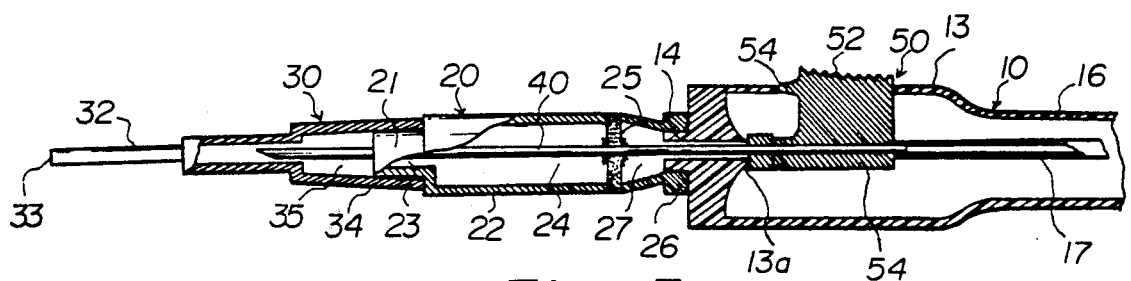
FIG. 5 is a side view of the catheter assembly of the present invention which includes a catheter needle sheath, catheter, and backflow device.

Another embodiment of the present invention is depicted in FIG. 5 which includes a catheter adapter and backflow device 20 which is engaged in a fluid tight manner to a catheter 30 and a catheter needle safety sheath 10. The adapter and backflow device 20 includes an adapter housing 22 having an adapter cavity 24 therein. The backflow device may be vented or nonvented (as shown). The housing 22 is formed preferably in a cylindrical shape from lightweight, transparent plastic material which is suitable for prolonged contact with human tissues and contact with blood and other therapeutic medical fluids. A front adapter end 21 is inserted in a fluid tight manner into a rearwardly opening hub member 34 of the catheter 30. A front adapter passageway 23 is in fluid communication with a catheter passageway 35. A rear adapter hub member 26 receives a tapered front end 14 of the catheter needle safety sheath 10. A rear adapter passageway 27 allows for introduction of the needle 40 therethrough.

Figure 6:
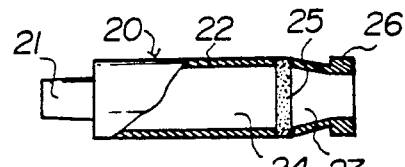
FIG. 6 is a side view of the backflow device of the present invention.

The catheter adaptor and backflow device 20 further includes a valve member 25 which is a soft elastomeric diaphragm disposed within the adapter housing 22. The elastomeric diaphragm may be formed from various elastomeric materials such as Latex, silicone, rubber, soft plastic, Neoprene, or suitable fibrous material, such as paper filter material. The elastomeric diaphragm 25 is easily punctured by a needle, such as the needle 40, to allow for extraction of blood and introduction of therapeutic fluids. Upon withdrawal of the needle from the elastomeric diaphragm 25, the diaphragm 25 re-seals to prevent further discharge of blood or fluids therethrough. The diaphragm 25 does not necessarily rely upon structural confinement for re-sealing, but rather re-seals by movement of the diaphragm material so as to return to its original position thereby filling the puncture opening which remains upon withdrawal of the needle. FIG. 6 illustrates a sideview of the catheter adapter and backflow device 20 disengaged from the rest of the catheter assembly.

Figure 7:
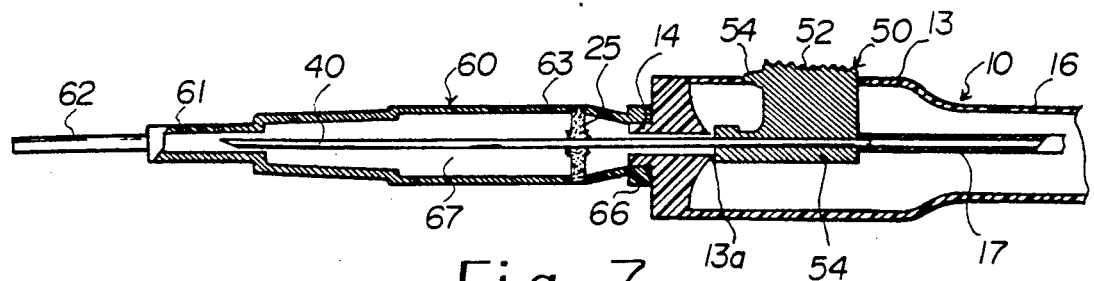
FIG. 7 is a side view of another embodiment of the present invention which includes a unitary catheter-backflow device and a catheter needle sheath.

FIG. 7 illustrates yet another embodiment of the present invention which includes a catheter needle safety sheath 10 engaged with a unitary catheter-backflow device 60. The tapered front end 14 of the needle sheath 10 is inserted into a rearwardly opening hub member 66 so that the needle 40 may project through a passageway 67 and into a plastic needle member 62. The housing 63 of the unitary catheter backflow device 60 includes a tapered front portion 61 and includes a self-closing valve member 25 that serves the same function and is formed from the same materials as described above with regard to the diaphragm 25.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An intravascular catheter assembly comprising:
   (a) a catheter member having a plastic needle tube for receiving a needle therethrough for insertion into a vein, a catheter passageway, and a rearwardly opening hub member;
   (b) a catheter adapter and backflow device having a front adapter end for insertion into said rearwardly opening hub member in a fluid tight manner, an adapter cavity within said backflow device for fluidly communicating with said catheter member, a rear adapter hub member, and a self-closing valve member for preventing fluid leakage from said catheter member which is disposed in said catheter adapter between said adapter cavity and said adapter hub member, said self-closing valve member comprising an elastomeric diaphragm which re-seals by a return of the diaphragm material to its original position so as to fill a puncture opening caused by a needle, wherein said backflow device receives a needle through said self-closing valve for fluid communication therewith; and,
   (c) a catheter needle safety sheath comprising:
      (i) an elongated hollow sheath housing having an elongated sheath slot formed therein and a tapered front end adapted for insertion into said rear adapter hub member;
      (ii) a retractable needle slidably disposed in said sheath housing;
      (iii) a needle hub member mounted on a rearward end of said needle;
      (iv) a fin-shaped handle mounted on said needle hub member, said handle projecting out of said sheath slot for slidably moving said needle so it projects out of said front end or retracts into said sheath housing; and,
      (v) a needle hub end member mounted on a rearward end of said needle hub member and slidably disposed within a rear portion of said sheath housing.

2. The intravascular catheter assembly of claim 1, wherein said catheter adapter and backflow device are cylindrical in shape and comprises lightweight transparent plastic material suitable for prolonged contact with human tissues and blood, and therapeutic medical fluids.

3. An intravascular catheter assembly comprising:
   (a) a catheter member having a plastic needle tube for receiving a needle therethrough for insertion into a vein, a catheter passageway, and a rearwardly opening hub member;
   (b) a catheter adapter and backflow device having a front adapter end for insertion into said rearwardly opening hub member in a fluid tight manner, an adapter cavity within said backflow device for fluidly communicating with said catheter member, a rear adapter hub member, and a self-closing valve member for preventing fluid leakage from said catheter member which is disposed in said catheter adapter between said adapter cavity and said adapter hub member, said self-closing valve member comprising an elastomeric diaphragm which re-seals by a return of the diaphragm material to its original position so as to fill a puncture opening caused by a needle, wherein said backflow device receives a needle through said self-closing valve for fluid communication therewith; and,
   (c) a catheter needle safety sheath comprising:
      (i) an elongated hollow sheath housing having an elongated sheath slot formed therein and a tapered front end adapted for insertion into said rear adapter hub member;
      (ii) a retractable needle slidably disposed in said sheath housing;
      (iii) a needle hub member mounted on a rearward end of said needle; and,
      (iv) a tab-shaped handle including a roughened upper surface mounted on said needle hub member.

4. The catheter needle safety sheath housing of claim 3, further comprising:
   (a) a wedge member disposed on the front portion of said tab-shaped handle member for frictionally engaging a front tapered portion of said elongated sheath slot; and,
   (b) a retraction hole disposed at the front inner surface of said sheath housing for allowing said needle to retract therethrough and for preventing said needle to again project therethrough.

5. The intravascular catheter assembly of claim 4, wherein said handle includes two slide slots for slidably engaging said sheath housing.

* * * * *